(12) United States Patent
Lebofsky et al.

(10) Patent No.: US 11,834,655 B2
(45) Date of Patent: *Dec. 5, 2023

(54) MOLECULAR BARCODING

(71) Applicant: Bio-Rad Laboratories, Inc., Hercules, CA (US)

(72) Inventors: Ronald Lebofsky, Kensington, CA (US); Jeremy Agresti, Richmond, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 30 days.

This patent is subject to a terminal disclaimer.

(21) Appl. No.: 17/565,249

(22) Filed: Dec. 29, 2021

(65) Prior Publication Data

US 2022/0112488 A1    Apr. 14, 2022

Related U.S. Application Data

(60) Continuation of application No. 16/927,690, filed on Jul. 13, 2020, now Pat. No. 11,248,227, which is a division of application No. 15/984,905, filed on May 21, 2018, now Pat. No. 10,752,894.

(60) Provisional application No. 62/510,095, filed on May 23, 2017.

(51) Int. Cl.
| | | |
|---|---|---|
| C12N 5/10 | (2006.01) | |
| C12Q 1/6806 | (2018.01) | |
| C12N 15/10 | (2006.01) | |
| C12Q 1/6869 | (2018.01) | |
| C12Q 1/6809 | (2018.01) | |

(52) U.S. Cl.
CPC ....... *C12N 15/1065* (2013.01); *C12Q 1/6806* (2013.01); *C12Q 1/6809* (2013.01); *C12Q 1/6869* (2013.01); *C12Q 2563/185* (2013.01)

(58) Field of Classification Search
CPC .......... C12N 15/1065; C12Q 1/6806; C12Q 1/6809; C12Q 1/6869; C12Q 2563/185
See application file for complete search history.

(56) References Cited

U.S. PATENT DOCUMENTS

2012/0237943 A1*  9/2012  Soldatov ............. C12Q 1/6876
                                                        435/6.19
2016/0289740 A1*  10/2016  Fu ........................ C12Q 1/6806

FOREIGN PATENT DOCUMENTS

| WO | 2012/116661 A1 | 9/2012 | |
|---|---|---|---|
| WO | 2013/085710 A2 | 6/2013 | |
| WO | 2016/003814 A1 | 1/2016 | |
| WO | WO-2016003814 A1 * | 1/2016 | ............. C12N 15/10 |

OTHER PUBLICATIONS

International Search Report and Written Opinion in PCT/US2018/033653 dated Sep. 3, 2018; 12 pages.

Caruccio, N. et al.; "Nextera™ Technology for NGS DNA Library Preparation: Simultaneous Fragmentation and Tagging by In Vitro Transposition"; retrieved from the internet http://www.epibio.com/docs/default-source/forum-archive/forum-16-3---nextera-technology-for-ngs-dna-library-preparation---simultaneous-fragmentation-and-tagging-by-in-vitro-transposition.pdf?sfvrsn=4; Oct. 1, 2009; 3 pages.

Head, S.R. et al.; "Library construction for next-generation sequencing: Overview and Challenges"; Biotechniques; vol. 56, No. 2; Feb. 1, 2014; pp. 61-77.

Islam, S. et al.; "Quantitative single-cell RNA-seq with unique molecular identifiers" and "Supplementary Figures and Note"; Nature Methods; vol. 11, No. 2; Feb. 2014; pp. 163-168 and 16 additional pages.

Kinde, I. et al.; "Detection and quantification of rare mutations with massively parallel sequencing" and "Supporting Information"; PNAS; vol. 108, No. 23; Jun. 7, 2011; pp. 9530-9535 and 10 additional pages..

* cited by examiner

*Primary Examiner* — Sahana S Kaup
(74) *Attorney, Agent, or Firm* — Kilpatrick Townsend and Stockton LLP

(57) ABSTRACT

Methods and compositions are provided for making and using uniquely tagged target nucleic acid molecules.

8 Claims, 7 Drawing Sheets

Specification includes a Sequence Listing.

Sequencing primer

Which sequence length gets inserted here is random

THUS, ASSUMING THAT:
1) Termination seqs due to random tagmentation provides us with >200 (conservative) "termination" barcodes
2) The 5 base stagger provides us with an additional 5 barcodes.

WE HAVE 1000 (conservative) MOLECULAR BARCODES BASED ON THESE 2 SOURCES.

- 8 less bases to do what you want with (sequencing)
- less gel bead oligo randomness to improve specificity during RT and PCR
- Takes advantage of no PCR pre nextera in the second strand direct approach (unique proposition to our platform)

FIG. 7

SEQUENCE LISTING

<160> NUMBER OF SEQ ID NOS: 7

<210> SEQ ID NO 1
<211> LENGTH: 150
<212> TYPE: DNA
<213> ORGANISM: Artificial Sequence

```
<220> FEATURE:
<223> OTHER INFORMATION: synthetic barcode tag sequence
<220> FEATURE:
<221> NAME/KEY: misc_feature
<222> LOCATION: (1)..(1)
<223> OTHER INFORMATION: T linked to Bead at N-terminus
<220> FEATURE:
<221> NAME/KEY: misc_feature
<222> LOCATION: (25)..(536)
<223> OTHER INFORMATION: sequencing primer oligonucleotides
<220> FEATURE:
<221> NAME/KEY: misc_feature
<222> LOCATION: (54)..(58)
<223> OTHER INFORMATION: N = A, C, G, or T; N may be present or absent
<220> FEATURE:
<221> NAME/KEY: misc_feature
<222> LOCATION: (59)..(64)
<223> OTHER INFORMATION: N = A, C, G, T, or U
<220> FEATURE:
<221> NAME/KEY: misc_feature
<222> LOCATION: (80)..(85)
<223> OTHER INFORMATION: N = A, C, G, T, or U
<220> FEATURE:
<221> NAME/KEY: misc_feature
<222> LOCATION: (101)..(106)
<223> OTHER INFORMATION: N = A, C, G, T, or U
<220> FEATURE:
<221> NAME/KEY: misc_feature
<222> LOCATION: (110)..(117)
<223> OTHER INFORMATION: N = A, C, G, or T

<400> SEQUENCE: 1
tttttttuuu ctacacgcct gtccgcggaa gcagtggtat caacgcagag tacnnnnnn      60 nnnntagcca tcgcattgcn nnnnntacca ctgagctgaa nnnnnnacgn nnnnnnngac    120
tttttttttt tttttttttt tttttttttt                                     150

<210> SEQ ID NO 2
<211> LENGTH: 15
<212> TYPE: DNA
<213> ORGANISM: Artificial Sequence
<220> FEATURE:
<223> OTHER INFORMATION: synthetic oligonucloetide sequence

<400> SEQUENCE: 2
gtctcgtggg ctcgg                                                      15

<210> SEQ ID NO 3
<211> LENGTH: 14
<212> TYPE: DNA
<213> ORGANISM: Artificial Sequence
<220> FEATURE:
<223> OTHER INFORMATION: synthetic oligonucloetide sequence

<400> SEQUENCE: 3
tcgtcggcag cgtc                                                       14

<210> SEQ ID NO 4
<211> LENGTH: 19
<212> TYPE: DNA
<213> ORGANISM: Artificial Sequence
<220> FEATURE:
<223> OTHER INFORMATION: synthetic oligonucloetide sequence

<400> SEQUENCE: 4
agatgtgtat aagagacag                                                  19

<210> SEQ ID NO 5
<211> LENGTH: 33
<212> TYPE: DNA
```

```
<213> ORGANISM: Artificial Sequence
<220> FEATURE:
<223> OTHER INFORMATION: synthetic oligonucloetide sequence

<400> SEQUENCE: 5
tcgtcggcag cgtcagatgt gtataagaga cag                        33

<210> SEQ ID NO 6
<211> LENGTH: 34
<212> TYPE: DNA
<213> ORGANISM: Artificial Sequence
<220> FEATURE:
<223> OTHER INFORMATION: synthetic oligonucloetide sequence

<400> SEQUENCE: 6
gtctcgtggg ctcggagatg tgtataagag acag                       34

<210> SEQ ID NO 7
<211> LENGTH: 19
<212> TYPE: DNA
<213> ORGANISM: Artificial Sequence
<220> FEATURE:
<223> OTHER INFORMATION: synthetic oligonucloetide sequence

<400> SEQUENCE: 7
ctgtctctta tacacatct                                        19
```

MOLECULAR BARCODING

RELATED APPLICATIONS

This application is a continuation application of U.S. application Ser. No. 16/927,690, filed Jul. 13, 2020, which is a divisional of U.S. application Ser. No. 15/984,905 filed on May 21, 2018, now U.S. Pat. No. 10,752,894, which claims the benefit of U.S. Provisional Application 62/510,095 filed on May 23, 2017, each of which is hereby incorporated by reference in its entirety.

REFERENCE TO A "SEQUENCE LISTING" SUBMITTED AS ASCII TEXT FILES VIA EFS-WEB

The Sequence Listing written in file SEQ_094868-1291261-113230US.txt created on Dec. 29, 2021, 2,509 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Next generation sequencing technology can provide enormous amounts of sequence information from a relatively small sample, such as a sample of nucleic acid (e.g., mRNA) from a single cell. However, it can be difficult to extract quantitative information regarding the absolute or relative abundance of nucleic acids in a sample. In some cases, the attachment of unique molecular identifiers (UMIs), such as unique oligonucleotide barcode sequences, to target nucleic acids, and detection of such UMIs during sequencing, can allow estimation of absolute or relative abundance of target nucleic acids in a sample.

BRIEF SUMMARY OF THE INVENTION

In one aspect, the present invention provides a method for producing a reaction mixture comprising uniquely tagged target nucleic acid molecules, the method comprising: (a) covalently linking a plurality of variable length barcode tags consisting of from 0-10 nucleotides of one or more nucleic acid sequence(s) to a first end of a plurality of target nucleic acid molecules, such that individual target nucleic acid molecules of the plurality comprise a single variable length barcode tag and the plurality comprises at least 5 different variable length barcode tag lengths and/or sequence(s); and (b) contacting the target nucleic acid molecules with a plurality of transposases, such that a transposase fragmentation site and a covalently linked transposon end is introduced at a second end of the individual target nucleic acid molecules of the plurality, thereby producing a plurality of uniquely tagged target nucleic acid molecules, wherein individual uniquely tagged target nucleic acid molecules of the plurality comprise: (i) the variable length barcode tag at the first end; and (ii) the transposase fragmentation site and transposon end at the second end, wherein a combination of: (i) and (ii) together in the uniquely tagged individual target nucleic acid molecules of the plurality comprise a unique molecular barcode that is unique as compared to all other uniquely tagged individual target nucleic acid molecules of the plurality that have an identical sequence of at least 25 contiguous nucleotides between the variable length barcode tag and the transposase fragmentation site in the reaction mixture. In some embodiments, the reaction mixture comprises at least 1,000 target nucleic acid molecules of different sequence.

In some embodiments, covalently linking a plurality of variable length barcode tags comprises hybridizing a plurality of primers that comprise the variable length barcode tag with a plurality of nucleic acid molecules comprising at least a portion of target nucleic acid molecule sequence, and extending the primers with a polymerase, thereby producing a plurality of double-stranded variable length barcode-tagged target nucleic acid molecules. In some embodiments, covalently linking a plurality of variable length barcode tags comprises ligating the variable length barcode tags to the target nucleic acid molecules of the plurality.

In some embodiments the plurality of nucleic acid molecules comprise mRNA and the polymerase is an RNA-dependent DNA polymerase. In another embodiment, the plurality of nucleic acid molecules comprise mRNA and the plurality of primers that comprise the variable length barcode tag comprise a 3' oligo-dT end.

In some embodiments, the first end of the target nucleic acid molecules comprises a poly-A region. In another embodiment, the first end of the uniquely tagged target nucleic acid molecules comprises a poly-A region and/or a poly-T region. In some embodiments, the variable length barcode tag is 3' of the poly-A region and/or 5' of the poly-T region.

In some embodiments, the method includes after step (a) and before step (b), forming variable length barcode tagged double-stranded target nucleic acid molecules comprising a first DNA strand hybridized to a reverse complementary second DNA strand. In another embodiment, the variable length barcode tagged double-stranded target nucleic acid molecules comprise double-stranded target cDNA molecules.

In some embodiments, the variable length barcode tagged double-stranded target nucleic acid molecules comprise variable length barcode tagged target genomic DNA molecules. In some embodiments, the method includes producing the variable length barcode tagged target genomic DNA molecules by hybridizing a plurality of first primers that comprise the variable length barcode tag and a genomic DNA targeting region with a plurality of genomic DNA molecules comprising at least a portion of the target nucleic acid molecule sequence, and extending the primers with a DNA-dependent DNA polymerase, thereby producing the variable length barcode tagged target genomic DNA molecules. In some embodiments, the method comprises amplifying the variable length barcode tagged target genomic DNA molecules.

In one aspect, the present invention provides a method of forming double-stranded target cDNA molecules by: (i) hybridizing a plurality of individual primers, wherein the individual primers comprise a variable length barcode tag with a plurality of mRNA molecules, and extending the primers with an RNA-dependent DNA polymerase, thereby producing a plurality of double-stranded mRNA:cDNA hybrids comprising first strand cDNA molecules hybridized to mRNA molecules; (ii) contacting the mRNA:cDNA hybrids with an enzyme comprising RNase H activity, thereby producing mRNA fragments hybridized to the first strand cDNA molecules; and (iii) contacting the mRNA fragments with a DNA-dependent DNA polymerase, thereby extending the mRNA fragments in a template-directed polymerase reaction, wherein the template is the first strand cDNA polynucleotide and forming the double-stranded target cDNA molecules. In some embodiments, the method comprises contacting the double-stranded target cDNA molecules with a ligase.

In some embodiments, the RNA-dependent DNA polymerase comprises RNase H activity. In some embodiments, the method comprises contacting the mRNA:cDNA hybrids with the enzyme comprising RNase H activity and incubating the mRNA:cDNA hybrids in the presence of the RNA-dependent DNA polymerase to thereby produce the mRNA fragments hybridized to the first strand cDNA molecules. In some embodiments, contacting the mRNA:cDNA hybrids with the enzyme comprising RNase H activity comprises contacting the mRNA:cDNA hybrids with an enzyme that is structurally different from the RNA-dependent DNA polymerase.

In some embodiments, the method of producing a reaction mixture comprising uniquely tagged nucleic acid molecules including steps (i) and (ii) together comprise a unique molecular identifier for an individual target nucleic acid molecule sequence, and the plurality of uniquely tagged individual target nucleic acid molecules do not comprise any other unique molecular identifier. In some embodiments, the plurality of uniquely tagged individual target nucleic acid molecules comprise a cell barcode. In some embodiments, the plurality of uniquely tagged individual target nucleic acid molecules are cDNA and the cell barcode is 3' of a poly-A region and/or 5' of a poly-T region.

In some embodiments, step (a) is performed in a reaction mixture wherein the target nucleic acid molecules are from a single cell. In some embodiments, steps (a) and (b) are performed in a reaction mixture wherein the target nucleic acid molecules are from a single cell. In some embodiments, step (b) is performed in a reaction mixture wherein the target nucleic acid molecules are from at least 10 cells. In another embodiment, step (b) is performed in a reaction mixture wherein the target nucleic acid molecules are from about 50 to about 500 cells. In one embodiment, step (b) is performed in a reaction mixture wherein the target nucleic acid molecules are from about 10 to about 5000 cells. In another embodiment, step (b) is performed in a reaction mixture wherein the target nucleic acid molecules are from about 10 to about 10000 cells.

In some embodiments, the variable length barcode tag consists of from 0-10 nucleotides of a single nucleic acid sequence, wherein at least a portion of variable length barcode tags contain at least 1 nucleotide.

In another embodiment, the variable length barcode tag consists of from 0-5 nucleotides, wherein at least a portion of variable length barcode tags contain at least 1 nucleotide.

In some embodiments, method step (a) is performed and then step (b) is performed on a plurality of double-stranded variable length barcode-tagged target nucleic acid molecules produced in method step (a) with or without an intervening amplification step.

In some embodiments, the transposon end comprises from 5' to 3' GTCTCGTGGGCTCGG (SEQ ID NO:2) or from 5' to 3' TCGTCGGCAGCGTC (SEQ ID NO:3).

In some embodiments, the transposon end comprises from 5' to 3' AGATGTGTATAAGAGACAG (SEQ ID NO:4).

In some embodiments, the transposon end comprises from 5' to 3' TCGTCGGCAGCGTCAGATGTGTATAAGAGACAG (SEQ ID NO:5).

In some embodiments, the transposon end comprises from 5' to 3' GTCTCGTGGGCTCGGAGATGTGTATAAGAGACAG (SEQ ID NO:6).

In some embodiments, the method further comprises after step (b), amplifying the uniquely tagged target nucleic acid molecules having the variable length barcode tag at the first end and the transposase fragmentation site and transposon end at the second end. In some embodiments, the amplification is performed with a hot-start DNA-dependent DNA polymerase. In some embodiments, the amplification is performed under conditions such that polymerase mediated nucleic acid extension substantially occurs after an initial denaturing step.

In one aspect, the present invention provides a method of estimating a number of target nucleic acid molecules in a reaction mixture, the method comprising: (A) providing the reaction mixture, wherein the reaction mixture comprises a plurality of uniquely tagged target nucleic acid molecules comprising: (i) a variable length barcode tag at a first end; and (ii) a transposase fragmentation site and transposon end at a second end; and wherein a combination of: (i) and (ii) together comprise a unique molecular barcode that is unique as compared to all other uniquely tagged target nucleic acid molecules having an identical sequence of at least 25 contiguous nucleotides between the variable length barcode tag and the transposase fragmentation site in the reaction mixture; (B) obtaining a plurality of sequence reads, wherein the sequence reads comprise one or more of the following: a sequence of the variable length barcode tag, a sequence of a portion of the target nucleic acid between the variable length barcode tag and the transposase fragmentation site, and a sequence of the fragmentation site; and (C) counting a number of target nucleic acid molecules having an identical sequence of at least 25 contiguous nucleotides between the variable length barcode tag and the transposase fragmentation site, but different variable length barcode tags and/or transposase fragmentation sites, thereby estimating the number of target nucleic acid molecules in the reaction mixture.

In some embodiments, the method of estimating a number of target nucleic acid molecules in a reaction mixture is performed according to any of the methods disclosed herein.

In some embodiments, the method of estimating a number of target nucleic acid molecules in a reaction mixture further includes after step (A) and before step (B), amplifying the target nucleic acid molecules having the variable length barcode tag at the first end.

In one aspect, the present invention provides a reaction mixture comprising a plurality of uniquely tagged target nucleic acid molecules, wherein the plurality of uniquely tagged target nucleic acid molecules comprise: (i) a variable length barcode tag at a first end; and (ii) a transposase fragmentation site and transposon end at a second end; and wherein a combination of: (i) and (ii) together comprise a unique molecular barcode that is unique as compared to all other uniquely tagged target nucleic acid molecules having an identical sequence between the variable length barcode tag and the transposase fragmentation site in the reaction mixture.

In some embodiments, the reaction mixture comprises at least 10 different uniquely tagged target nucleic acid molecules. In some embodiments, the reaction mixture comprises between 10 and 1000 different uniquely tagged target nucleic acid molecules, wherein the different uniquely tagged target nucleic acid molecules comprises mRNA transcripts from a single cell. In some embodiments, the reaction mixture comprises between 10 and 2000 different uniquely tagged target nucleic acid molecules, wherein the different uniquely tagged target nucleic acid molecules comprises mRNA transcripts from a single cell. In some embodiments, the reaction mixture comprises between 10 and 5000 different uniquely tagged target nucleic acid molecules, wherein the different uniquely tagged target nucleic acid molecules comprises mRNA transcripts from a single cell. In some embodiments, the reaction mixture comprises at least 10 different uniquely tagged target nucleic acid molecules, wherein the different uniquely tagged target nucleic acid molecules comprise unique mRNA transcripts from a single cell. In some embodiments, the reaction mixture comprises between 10 and 5000 different uniquely tagged target nucleic acid molecules, wherein the different uniquely tagged target nucleic acid molecules comprises unique mRNA transcripts from a plurality of cells. In some embodiments, the reaction mixture comprises between 10 and 10000 different uniquely tagged target nucleic acid molecules, wherein the different uniquely tagged target nucleic acid molecules comprise unique mRNA transcripts from a plurality of cells. In some embodiments, the reaction mixture comprises a fluid partition. In some embodiments, the reaction mixture comprises a droplet. In some embodiments, the reaction mixture comprises a droplet from an emulsion, such as but not limited to, a water-in-oil emulsion. In another embodiment, the reaction mixture comprises a plurality of droplets, optionally wherein each droplet comprises between 0 and 5000 different uniquely tagged target nucleic acid molecules. In another embodiment, the reaction mixture comprises a plurality of fluid partitions, wherein one or more of the fluid partitions comprises between 10 and 1000 different uniquely tagged target nucleic acid molecules, wherein the different uniquely tagged target nucleic acid molecules comprise unique mRNA transcripts from a single cell. In some embodiments, the reaction mixture further comprises amplification products of the uniquely tagged target nucleic acid molecules.

In one aspect, the present invention provides a computer program product comprising a non-transitory machine readable medium storing program code that, when executed by one or more processors of a computer system, causes the computer system to implement a method for estimating a number of target nucleic acid molecules in a reaction mixture using: (A) a sequence of the target nucleic acid; and (i) a variable length barcode tag at a first end of the target nucleic acid; and, (ii) a transposase fragmentation site and transposon end at a second end of the target nucleic acid to identify and estimate the number of individual molecules of the target nucleic acid in the reaction mixture, said program code comprising: code for obtaining reads of a plurality of amplified polynucleotides, wherein the plurality of amplified polynucleotides are obtained by amplifying nucleic acid fragments in the reaction mixture that comprise the variable length barcode tag at the first end; and, (ii) the transposase fragmentation site and transposon end at the second end; code for identifying a plurality of physical unique molecular identifiers (UMIs) in a combination of the variable length barcode tag and transposase fragmentation site;

and code for counting a number of target nucleic acid molecules having unique molecular identifiers.

BRIEF DESCRIPTION OF THE DRAWINGS

FIG. 7 lists several advantages to the approach outlined in FIGS. 4-6.

DEFINITIONS

Figure 1:
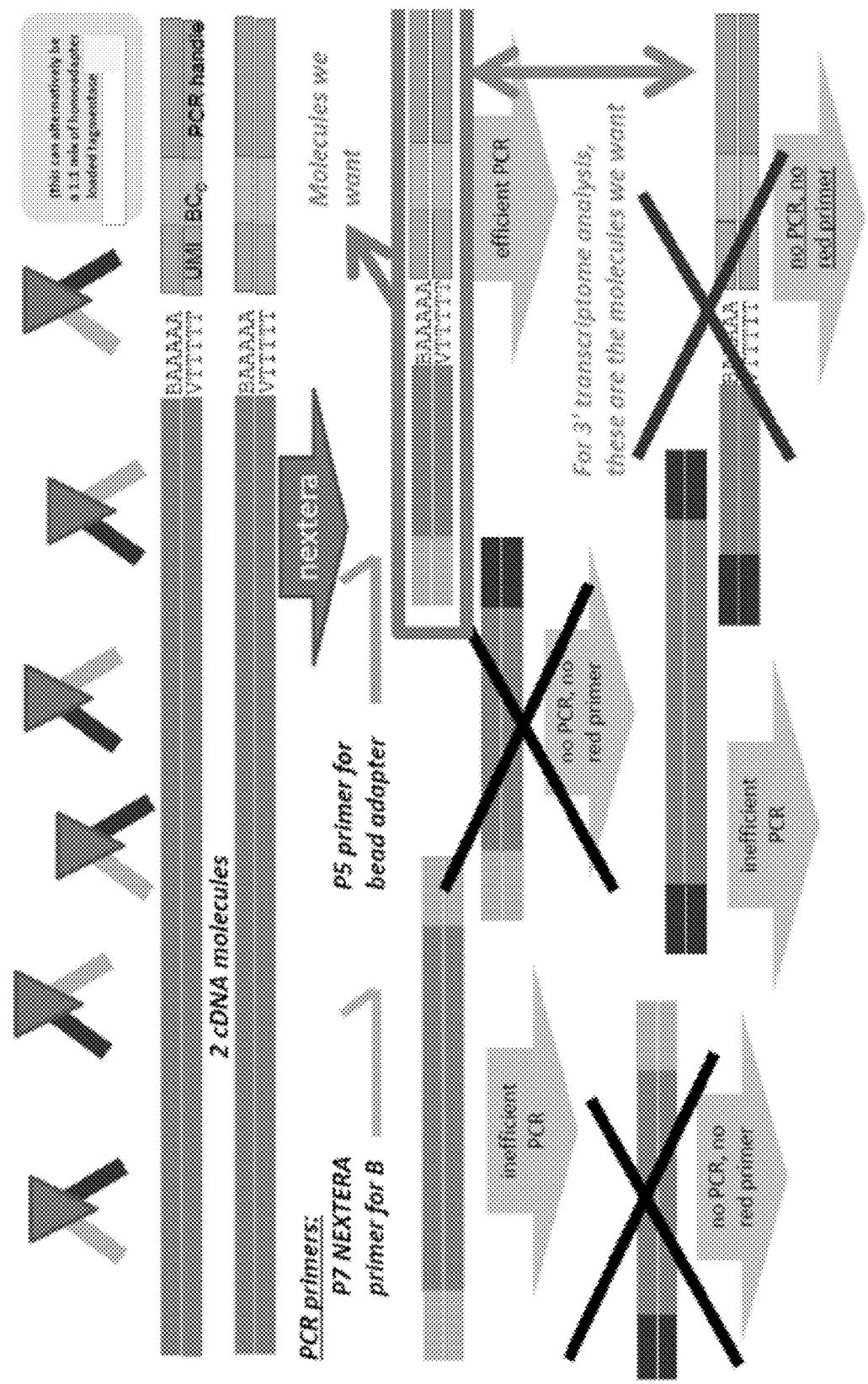
FIG. 1 illustrates methods and compositions for generating cDNA fragments having a transposon end introduced by a transposase at one end and a unique molecular identifier (UMI) barcode at a second end, where the second end contains a poly-A and poly-T region. The illustrated cDNA fragments further contain a cell barcode (BCS) and a PCR "handle" (PCR primer binding site) at the second end, as well as a compatible PCR primer binding site at the first end that is introduced by the transposase.
Figure 2:
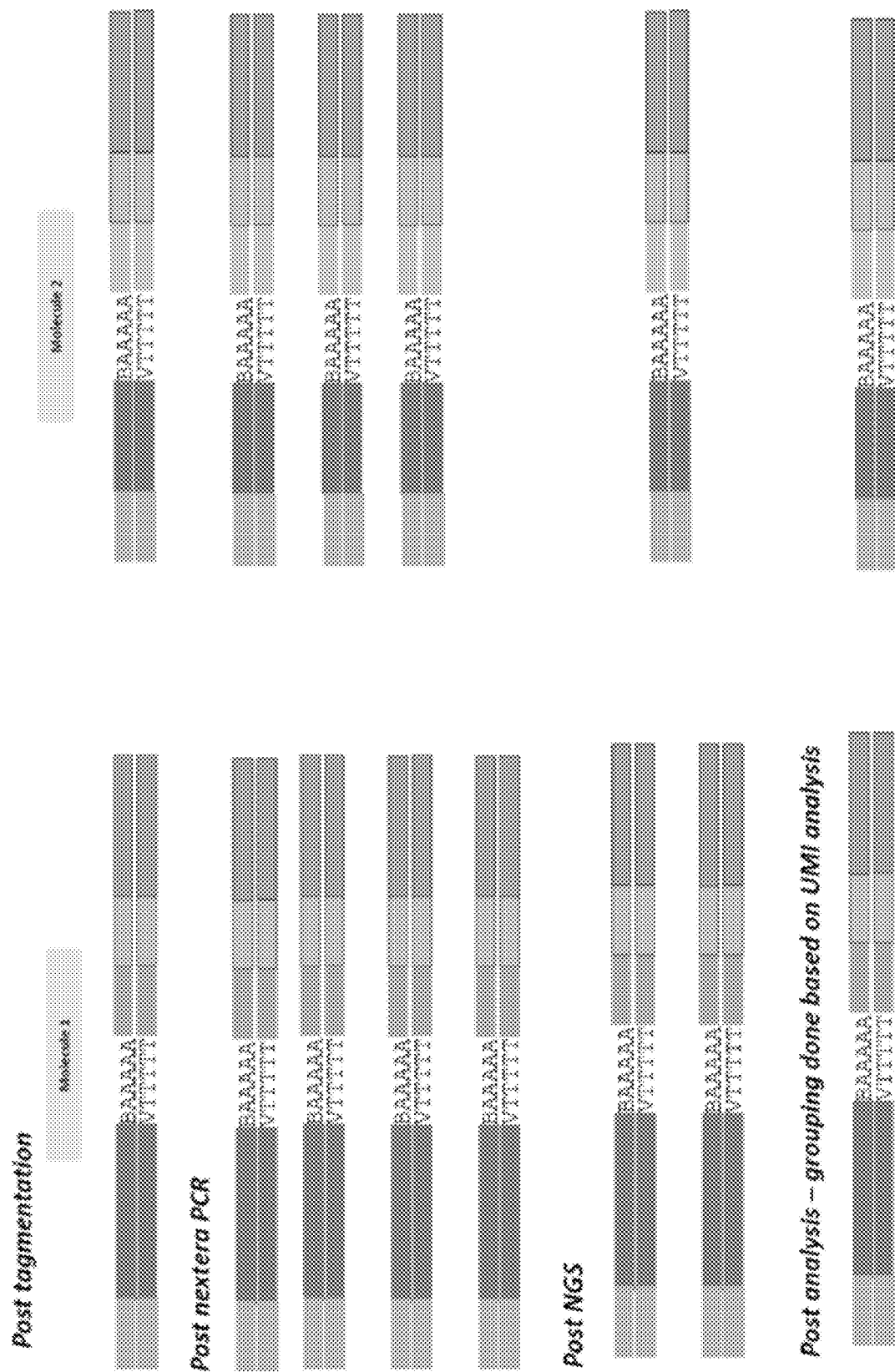
FIG. 2 illustrates a method for analyzing sequence reads of a library of the cDNA fragments illustrated in FIG. 1.
Figure 3:
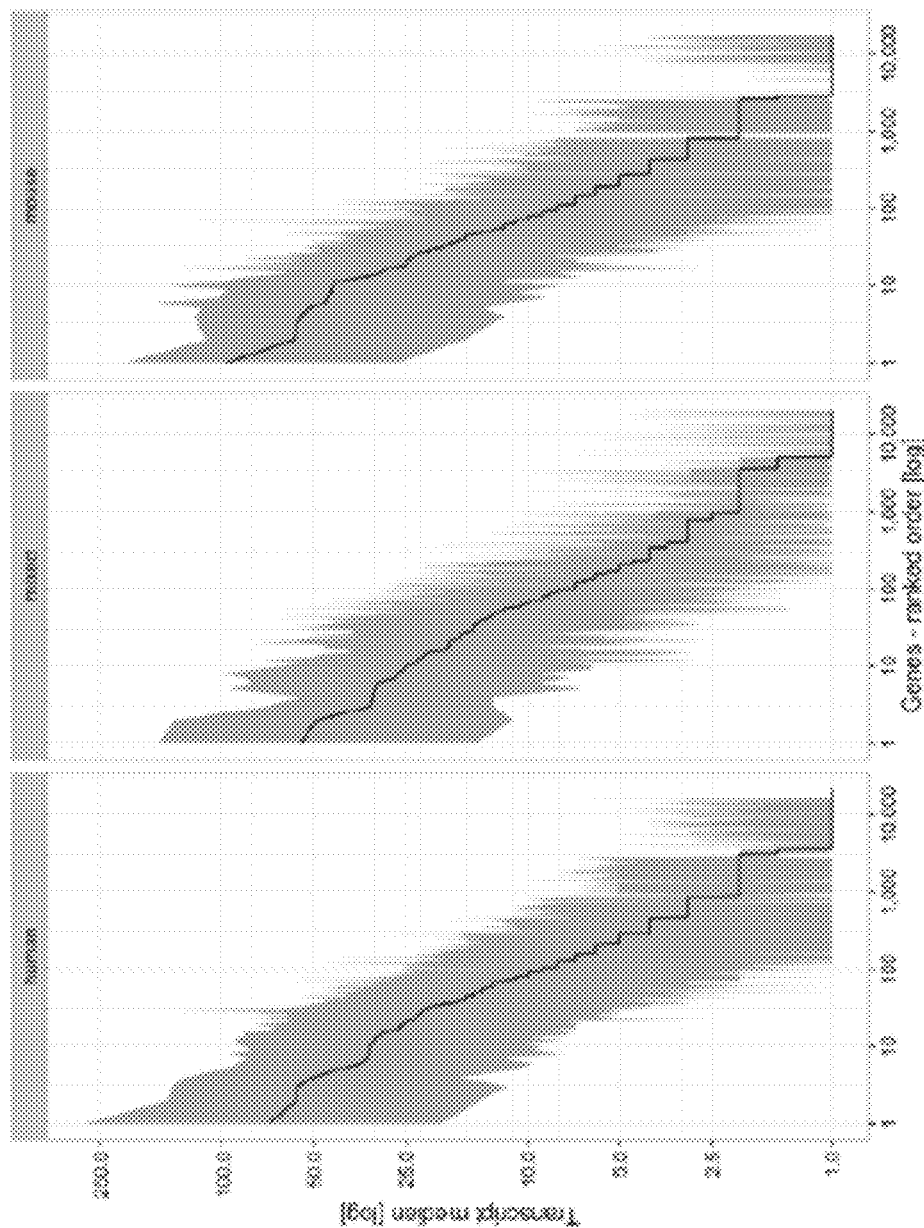
FIG. 3 illustrates a histogram analysis of transcript copy numbers found in a single human cell (left), mouse cell (right), and sample containing a mixture of human and mouse nucleic acid (center).
Figure 4:
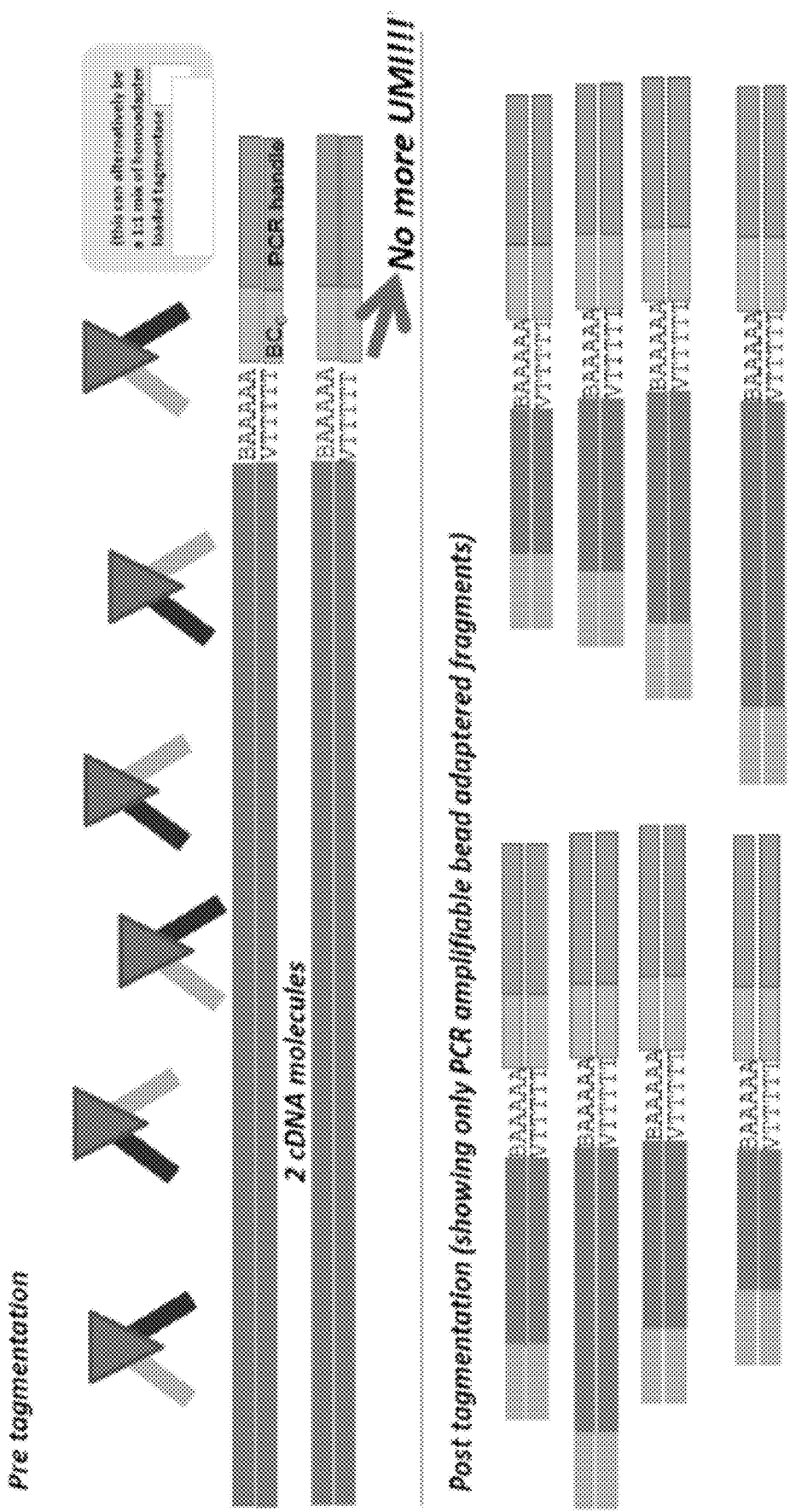
FIG. 4 illustrates an embodiment of the invention in which the UMI barcode is not present in the cDNA fragments generated by poly-T primer extension and transposase-mediated fragmentation. The variable position of the transposase fragmentation site can provide barcode diversity.
Figure 5:
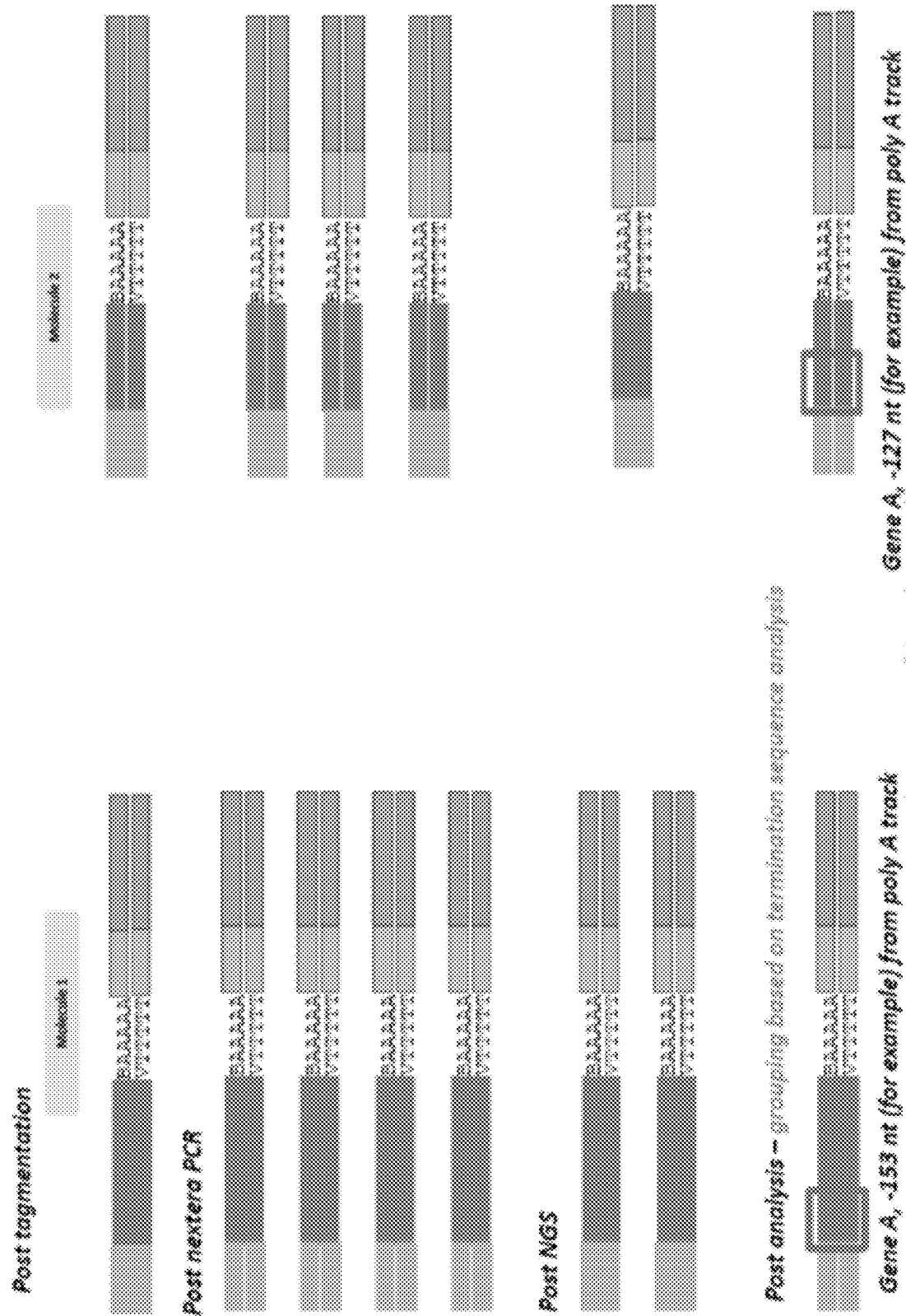
FIG. 5 illustrates a method for analyzing sequence reads of a library of the cDNA fragments illustrated in FIG. 4.
Figure 6:
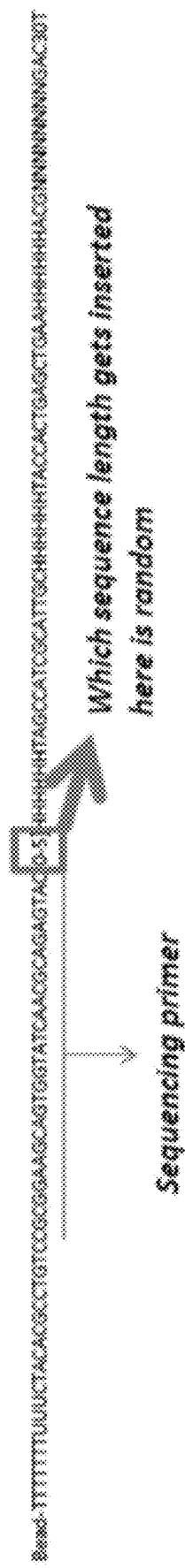
FIG. 6 illustrates the use of a variable length barcode tag (SEQ ID NO:1) having 0-5 nucleotides to increase the number of unique identifiers provided by transposase fragmentation by 6-fold. It is conservatively estimated that the combination of a variable length barcode tag and variable position of the transposase fragmentation site can provide at least 1,000 unique molecular identifiers.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "amplification reaction" refers to any in vitro means for multiplying the copies of a target sequence of nucleic acid in a linear or exponential manner. Such methods include but are not limited to two-primer methods such as polymerase chain reaction (PCR); ligase methods such as DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3 SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification. In an exemplary embodiment, amplifying refers to PCR amplification using a first and a second amplification primer.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds., 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are 0, or fewer than 2 or 3 complementarity mismatches over at least about 12, 14, 16, 18, or 20 contiguous nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C.

A "template" refers to a polynucleotide sequence that comprises the polynucleotide to be amplified, adjacent to a primer hybridization site, or flanked by a pair of primer hybridization sites. Thus, a "target template" comprises the target polynucleotide sequence adjacent to at least one hybridization site for a primer. In some cases, a "target template" comprises the target polynucleotide sequence flanked by a hybridization site for a "forward" primer and a "reverse" primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga maritime*, or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel or microwell. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

In some cases partitions are virtual. In a preferred embodiment, virtual partitions require a physical alteration of a molecule or group of molecules, wherein the alteration identifies a unique partition for that molecule or group of molecules. Typical physical alterations suitable for establishing or maintaining virtual partitioning include, without limitation, nucleic acid barcodes, detectable labels, etc. For example, a sample can be physically partitioned, and the components of each partition tagged with a partition-specific identifier (e.g., a nucleic acid barcode sequence) such that the identifier is unique as compared to other partitions but shared between the components of the partition. The partition-specific identifier can then be used to maintain a virtual partition in downstream applications that involve combining of the physically partitioned material. Thus, if the sample is a sample of cells physically partitioned into partitions containing a single cell, the identifier can identify different nucleic acids that derived from a single cell after partitions are recombined.

As used herein, a "tag" refers to a non-target nucleic acid component, generally DNA, that provides a means of addressing a nucleic acid fragment to which it is joined. For example, in preferred embodiments, a tag comprises a nucleotide sequence that permits identification, recognition, and/or molecular or biochemical manipulation of the DNA to which the tag is attached (e.g., by providing a unique or partition-specific sequence, and/or a site for annealing an oligonucleotide, such as a primer for extension by a DNA polymerase, or an oligonucleotide for capture or for a ligation reaction). The process of joining the tag to the DNA molecule is sometimes referred to herein as "tagging" and DNA that undergoes tagging or that contains a tag is referred to as "tagged" (e.g., "tagged DNA")." A tag can be a barcode, an adapter sequence, a primer hybridization site, or a combination thereof.

As used herein a "barcode" is a short nucleotide sequence (e.g., about 1, 2, 3, 4, 5, 6, 7, 8, 9, 10, 11, or 12 nucleotides long) that identifies a molecule to which it is conjugated. Barcodes can be used, for example, to identify molecules in a reaction mixture or partition. Generally, a partition-specific barcode should be unique for that partition as compared to barcodes present in other partitions. For example, partitions containing target RNA from single-cells can be subject to reverse transcription conditions using primers that contain a different partition-specific barcode sequence in each partition, thus incorporating a copy of a unique "cellular barcode" into the reverse transcribed nucleic acids of each partition. Thus, nucleic acids from each cell can be distinguished from nucleic acid of other cells due to the presence of the unique "cellular barcode." In some cases, the cellular barcode is provided as a "particle barcode" that is present on oligonucleotides conjugated to a particle (e.g., a magnetic bead), wherein the particle barcode is shared by (e.g., identical or substantially identical amongst) all, or substantially all, of the oligonucleotides conjugated to that particle. Thus, cellular and particle barcodes can be present in a partition, attached to a particle, or bound to cellular nucleic acid as multiple copies of the same barcode sequence. Cellular or particle barcodes of the same sequence can be identified as deriving from the same cell, partition, or particle. Such partition-specific, cellular, or particle barcodes can be generated using a variety of methods, which methods can result in the barcode conjugated to or incorporated into a solid or hydrogel support (e.g., a solid bead or particle or hydrogel bead or particle). In some cases, the partition-specific, cellular or particle barcode is generated using a split and mix (also referred to as split and pool) synthetic scheme. A partition-specific barcode can be a cellular barcode and/or a particle barcode. Similarly, a cellular barcode can be a partition-specific barcode and/or a particle barcode. Additionally, a particle barcode can be a cellular barcode and/or a partition-specific barcode.

In other cases, barcodes uniquely identify the molecule to which it is conjugated. For example, by performing reverse transcription using primers that each contain a "unique molecular identifier" barcode. In still other examples, primers can be utilized that contain "partition-specific barcodes" unique to each partition, and "molecular barcodes" unique to each molecule. After barcoding, partitions can then be combined, and optionally amplified, while maintaining virtual partitioning. Thus, e.g., the presence or absence of a target nucleic acid (e.g., reverse transcribed nucleic acid) comprising each barcode can be counted (e.g. by sequencing) without the necessity of maintaining physical partitions. In some cases, the unique molecular identifier barcode is encoded by a contiguous sequence of nucleotides tagged to one end of a target nucleic acid.

In some cases, the unique molecular identifier barcode is encoded by a non-contiguous sequence. Non-contiguous UMIs can have a portion of the barcode at a first end of the target nucleic acid and a portion of the barcode at a second end of the target nucleic acid. In some cases, the UMI is a non-contiguous barcode containing a variable length barcode sequence at a first end and a second identifier sequence at a second end of the target nucleic acid. In some cases, the UMI is a non-contiguous barcode having a variable length barcode sequence at a first end and a second identifier sequence at a second end of the target nucleic acid, wherein the second identifier sequence is determined by a position of a transposase fragmentation event, e.g., a transposase fragmentation site and transposon end insertion event.

The length of the barcode sequence can determine how many unique samples can be differentiated. For example, a 1 nucleotide barcode can differentiate 4, or fewer, different samples or molecules; a 4 nucleotide barcode can differentiate $4^4$ or 256 samples or less; a 6 nucleotide barcode can differentiate 4096 different samples or less; and an 8 nucleotide barcode can index 65,536 different samples or less. Additionally, barcodes can be attached to both strands of a target nucleic acid molecule (e.g., gDNA or cDNA) either through barcoded primers for both first and second strand synthesis, through ligation, or in a tagmentation reaction.

In some cases, the barcode is a "variable length barcode." As used herein, a variable length barcode is an oligonucleotide that differs from other variable length barcode oligonucleotides in a population, by length, which can be identified by the number of contiguous nucleotides in the barcode. In some cases, additional barcode complexity for the variable length barcode can be provided by the use of variable nucleotide sequence, as described in the paragraphs above, in addition to the variable length.

In an exemplary embodiment, a variable length barcode can have a length of from 0 to no more than 5 nucleotides. Such a variable length barcode can be denoted by the term "[0-5]." In such an embodiment, it is understood that a population of target nucleic acids that are attached to such a variable length barcode is expected to include at least one target nucleic acid attached to a variable length barcode that has at least 1 nucleotide (e.g., attached to a variable length barcode having only 1, only 2, only 3, only 4, or only 5 nucleotides). In such an embodiment, it is further understood that a population of target nucleic acids that are attached to such a variable length barcode can include at least one target nucleic acid that contains no variable length barcode (i.e., a variable length barcode having a length of 0), and/or at least one target nucleic acid that contains a variable length barcode having only 1 nucleotide, and/or at least one target nucleic acid that contains a variable length barcode having only 2 nucleotides, and/or at least one target nucleic acid that contains a variable length barcode having only 3 nucleotides, and/or at least one target nucleic acid that contains a variable length barcode having only 4 nucleotides, and/or and at least one target nucleic acid that contains a variable length barcode having only 5 nucleotides. In such an embodiment, the [0-5] variable length barcode can uniquely identify (differentiate), by itself, 5 different target nucleic acid molecules of the same sequence. Further, in such an embodiment, the [0-5] variable length barcode can uniquely identify (differentiate) 5 different target nucleic molecules of a first sequence, 5 different target nucleic acid molecules of a second sequence, etc. for each different target nucleic acid sequence.

Typically, a population of variable length barcodes has the same number, or substantially the same number, of oligonucleotides of each length. For example, a population of variable length barcodes of length 0-5 can have oligonucleotides of each length in equal proportion. It is further understood that a population of skipped variable length barcodes can skip one or more lengths. Such a "skipped variable length barcode" can have, for exemplary purposes only, oligonucleotides of length 0, 1, 2, 4, and 5, but no oligonucleotides of length 3.

Barcodes are typically synthesized and/or polymerized (e.g., amplified) using processes that are inherently inexact. Thus, barcodes that are meant to be uniform (e.g., a cellular, particle, or partition-specific barcode shared amongst all barcoded nucleic acid of a single partition, cell, or bead) can contain various N-1 deletions or other mutations from the canonical barcode sequence. Thus, barcodes that are referred to as "identical" or "substantially identical" refer to barcodes that differ due to one or more errors in, e.g., synthesis, polymerization, or purification errors, and thus contain various N-1 deletions or other mutations from the canonical barcode sequence. Moreover, the random conjugation of barcode nucleotides during synthesis using e.g., a split and pool approach and/or an equal mixture of nucleotide precursor molecules as described herein, can lead to low probability events in which a barcode is not absolutely unique (e.g., different from all other barcodes of a population or different from barcodes of a different partition, cell, or bead). However, such minor variations from theoretically ideal barcodes do not interfere with the high-throughput sequencing analysis methods, compositions, and kits described herein. Therefore, as used herein, the term "unique" in the context of a particle, cellular, partition-specific, or molecular barcode encompasses various inadvertent N-1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is well known in the art, see for example Shiroguchi et al., Proc. Natl. Acad. Sci. USA., 2012 Jan. 24; 109(4):1347-52; and Smith et al., Nucleic Acids Research, 2010 Jul; 38(13)11:e142. Further methods and compositions for using barcode technology include those described in U.S. 2016/0060621.

A "transposase" or "tagmentase" means an enzyme that is capable of forming a functional complex with a transposon end-containing composition and catalyzing insertion or transposition of the transposon end-containing composition into the double-stranded target DNA with which it is incubated in an in vitro transposition reaction. Typically, the insertion or transposition results in fragmentation of the target DNA.

The term "transposon end" means a double-stranded DNA that contains or consists of the nucleotide sequences (the "transposon end sequences") that are necessary to form the complex with the transposase that is functional in an in vitro transposition reaction. A transposon end forms a "complex" or a "synaptic complex" or a "transposome complex" or a "transposome composition" with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a "transferred transposon end sequence" or "transferred strand" and a "non-transferred transposon end sequence," or "non-transferred strand" For example, one transposon end that forms a complex with a hyperactive Tn5 transposase (e.g., EZ-Tn5™ Transposase, EPICENTRE Biotechnologies, Madison, Wis., USA) that is active in an in vitro transposition reaction comprises a transferred strand that exhibits a "transferred transposon end sequence" as follows:

(SEQ ID NO: 4)
5' AGATGTGTATAAGAGACAG 3', and a non-transferred strand that exhibits a "non-transferred transposon end sequence" as follows:

(SEQ ID NO: 7)
5' CTGTCTCTTATACACATCT 3'.

The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In another example, a transposon end that forms a complex with a transposase that is active in an in vitro transposition reaction comprises a transferred strand that exhibits a "transferred transposon end sequence" as follows:

(SEQ ID NO: 5)
5'-TCGTCGGCAGCGTCAGATGTGTATAAGAGACAG-3';
or (SEQ ID NO: 6)
5'-GTCTCGTGGGCTCGGAGATGTGTATAAGAGACAG-3.

and a non-transferred strand that exhibits a "non-transferred transposon end sequence" as follows:

(SEQ ID NO: 7)
5' CTGTCTCTTATACACATCT 3'.

In some embodiments, a transposon end-containing composition comprises a transferred transposon end and a non-transferred transposon end that form a double-stranded nucleotide composition. In some embodiments, a transposon end comprises a double-stranded nucleotide composition having a nucleotide sequence necessary to form a functional complex with a transposase resulting in insertion of the transposon ends into one or more of the target nucleic acid molecules with which it is incubated in an in vitro transposition reaction. In some embodiments, the double-stranded nucleotide composition corresponding to the transposon end comprises from 5' to 3' AGATGTGTATAAGAGACAG (SEQ ID NO 4) and from 5' to 3' CTGTCTCTTATACA-CATCT (SEQ ID NO:7). In another embodiment, the double-stranded nucleotide composition corresponding to the transposon end comprises from 5' to 3' TCGTCGGCAGCGTCAGATGTGTATAAGAGACAG (SEQ ID NO:5) and from 5' to 3' CTGTCTCTTATACA-CATCT (SEQ ID NO:7). In yet another embodiment, the double-stranded nucleotide composition corresponding to the transposon end comprises from 5' to 3' GTCTCGTGGGCTCGGAGATGTGTATAAGAGACAG (SEQ ID NO:6) and from 5' to 3' CTGTCTCTTATACA-CATCT (SEQ ID NO:7).

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure.

A "transposon end composition" means a composition comprising a transposon end (i.e., the minimum double-stranded DNA segment that is capable of acting with a transposase to undergo a transposition reaction), optionally plus additional sequence or sequences 5'-of the transferred transposon end sequence and/or 3'-of the non-transferred transposon end sequence. For example, a transposon end attached to a tag is a "transposon end composition." In some embodiments, the transposon end composition comprises or consists of two transposon end oligonucleotides consisting of the "transferred transposon end oligonucleotide" or "transferred strand" and the "non-transferred strand end oligonucleotide," or "non-transferred strand" which, in combination, exhibit the sequences of the transposon end, and in which one or both strand comprise additional sequence.

The terms "transferred transposon end oligonucleotide" and "transferred strand" are used interchangeably and refer to the transferred portion of both "transposon ends" and "transposon end compositions," i.e., regardless of whether the transposon end is attached to a tag or other moiety. Similarly, the terms "non-transferred transposon end oligonucleotide" and "non-transferred strand" are used interchangeably and refer to the non-transferred portion of both "transposon ends" and "transposon end compositions." In some embodiments, a transposon end composition is a "hairpin transposon end composition." As used herein, a "hairpin transposon end composition" means a transposon end composition consisting of a single oligodeoxyribonucleotide that exhibits a non-transferred transposon end sequence at its 5'-end, a transferred transposon end sequence at its 3'-end, and an intervening arbitrary sequence between the non-transferred transposon end sequence and the transferred transposon end sequence that is sufficiently long to allow intramolecular stem-loop formation, such that the transposon end portion can function in an in vitro transposition reaction. In some embodiments, the 5'-end of the hairpin transposon end composition has a phosphate group in the 5'-position of the 5'-nucleotide. In some embodiments, the intervening arbitrary sequence between the non-transferred transposon end sequence and the transferred transposon end sequence of a hairpin transposon end composition provides a tag (e.g., including one or more tag domains) for a particular use or application.

As used herein, the term "transposase fragmentation site" refers to a position in a target nucleic acid at which a transposon end is covalently linked to a portion of the target nucleic acid and the target nucleic acid is fragmented. Transposase fragmentation is not entirely random, and exhibits a "slight bias toward AT-rich sequences (see, Goryshin et al., Proc. Natl. Acad. Sci. USA., (1998) 95:10716-10721). The term "transposase fragmentation site" is not limited to a single type of nucleotide (i.e., A or T) or a specific nucleotide location in the target nucleic acid (e.g., the $3^{rd}$ distal nucleotide from the 3' end) at which the transposon end is covalently linked to a portion of the target nucleic acid but instead refers to a nucleotide that corresponds to the position in the target nucleic acid at which the transposon end is covalently linked to a portion of the target nucleic acid because the location of the tagmentation reaction is somewhat random. The uniquely tagged individual target nucleic acid molecules include an identical sequence of at least 25 contiguous nucleotides between the variable length barcode tag and the transposase fragmentation site. Nevertheless, transposase fragmentation site selection is sufficiently unbiased such that, in combination with a variable length barcode tag, at least 50; 100; 200; 300; 400; 500; 1,000; 1,500; 2,000; 2,500; 3,000, or more different target nucleic acid molecules of a given sequence, or portion thereof (e.g., at least 25 contiguous nucleotides of a given target nucleic acid sequence), can be uniquely identified. Thus, for example, in a sample containing target nucleic acids that are mRNA transcripts of a genome of a single human cell, or cDNA therefrom, wherein 99% of unique transcript sequences or corresponding cDNA are present in fewer than 200 or 100 copies depending on sample preparation efficiencies, the transposase fragmentation site in combination with a variable length barcode tag having a length of from 0-5 or 0-10 nucleotides is sufficient to uniquely identify at least 90%, 91%, 92%, 93%, 94%, 95%, 96%, 97%, 98%, 99%, 99.5%, 99.9%, 99.95%, or 99.99% of the target nucleic acids.

The term "second end" as used in conjunction with an individual target nucleic acid molecule refers to a position in the individual target nucleic acid molecule at which the in vitro transposition reaction occurs. A "second end" does not refer to the actual, physical termination of the 3' or 5' end of the target nucleic acid molecule; rather the position at which insertion of the transposon end-containing composition into the double-stranded target nucleic acid molecule occurs. Completion of the in vitro transposition reaction creates a new end (i.e., second end) as a result of fragmentation of the double-stranded target nucleic acid molecule. As such, a second end refers to a position toward the 3' or 5' end of the individual target nucleic acid molecule underdoing in vitro transposition but not the actual, physical termination of the 3' or 5' end of the individual target nucleic acid molecule prior to in vitro transposition.

DETAILED DESCRIPTION OF THE INVENTION

I. Introduction

The present inventors have discovered that for a variety of samples, the use of transposase fragmentation and a variable length barcode tag (in combination) can provide a sufficient number of unique molecular identifier (UMI) barcodes to provide absolute or relative quantitation of substantially all (>90%, >93%, >95% or >99%) target nucleic acids in a sample by high-throughput sequencing. In some cases, the length and/or sequence of the variable length barcode in combination with the transposase fragmentation position can provide about 50; 100; 200; 300; 400; 500; 1,000; 1,500; 2,000; 2,500; 3,000, or more different barcodes for each target nucleic acid sequence in a sample. In some cases, this obviates the need for a separate UMI barcode sequence (for example, incorporated with a PCR primer) and thus allows for longer reads of target nucleic acid sequence as compared to methods in which a separate UMI barcode is used. In another aspect, the methods disclosed herein provide for fewer different random sequences in the PCR primer sequence, thus improving specificity during later steps of RT and/or PCR amplification.

II. Methods of Tagging

Thus, described herein is a method of producing a reaction mixture containing target nucleic acid sequences that have been tagged with a variable length barcode tag and a transposase fragmentation site. Typically, the variable length barcode tag is at a first end of a target nucleic acid and the transposase fragmentation site is at a second end of the target nucleic acid, although the order may be reversed. Alternatively, the variable length barcode and transposase fragmentation site can be at the same end of the target nucleic acid. In some cases, the variable length barcode tag is at a first end, wherein the first end comprises or corresponds to a 3' end of an mRNA (e.g., a 3' poly-A region) or a poly-T region of a cDNA.

In some embodiments, the method can include covalently linking a plurality of variable length barcode tags to a first end of a plurality of target nucleic acid molecules. Typically, the target nucleic acids have not been contacted and/or fragmented with a transposase prior to covalently linking the variable length barcode tag. Alternatively, the target nucleic acids can be fragmented with a transposase, e.g., thereby producing a fragment tagged with a transposon end composition at one end, and then covalently linked to a variable length barcode tag.

The variable length barcode tags can be (e.g., consist of) 0-2, 0-3, 0-4, 0-5, 0-6, 0-7, 0-8, 0-9, 0-10, 0-11, 0-12, 0-13, 0-14, or 0-15 nucleotides in length. The variable length barcode tags can be (e.g., consist of) 1-2, 1-3, 1-4, 1-5, 1-6, 1-7, 1-8, 1-9, 1-10, 1-11, 1-12, 1-13, 1-14, or 1-15 nucleotides in length. In some cases, the variable length barcode tags are 0-10 or 0-5 nucleotides in length. In some cases, the variable length barcode tags are 1-10 or 1-5 nucleotides in length.

The plurality of variable length barcode tags can be covalently linked to the plurality of target nucleic acid molecules by ligation with a ligase and/or polymerization. For example, the plurality of variable length barcode tags can be ligated to a target nucleic acid molecule that has been prepared for ligation at one or both ends by phosphorylation of 5' ends, de-phosphorylation of 3' ends, cleavage (e.g., endonuclease cleavage), tailing, end-repair, etc. As another example, the plurality of variable length barcode tags can be covalently linked to a target nucleic acid molecule by hybridizing a primer containing the variable length barcode tag to a portion of the target nucleic acid and extending the primer with a template dependent polymerase.

In some embodiments, the untagged, target nucleic acid molecules are mRNA and the method includes hybridizing a plurality of primers that comprise the variable length barcode tag, and optionally a poly-T 3' end, with a plurality of nucleic acid molecules comprising at least a portion of a target nucleic acid molecule sequence, and extending the primers with an RNA-dependent DNA polymerase, thereby producing a plurality of double-stranded variable length barcode-tagged target nucleic acid molecules. In some cases, the variable length barcode tag is 3' of the poly-A region and/or 5' of the poly-T region. In some cases, the method further comprises producing a plurality of double-stranded variable length barcode-tagged target cDNA molecules. For example, the method can include forming variable length barcode tagged double-stranded target nucleic acid molecules comprising a first DNA strand hybridized to a reverse complementary second DNA strand.

In some embodiments, producing double-stranded variable length barcode-tagged target cDNA molecules includes (i) hybridizing a plurality of individual primers, wherein the individual primers contain the variable length barcode tag with a plurality of mRNA molecules, and extending the primers with an RNA-dependent DNA polymerase, thereby producing a plurality of double-stranded mRNA:cDNA hybrids with first strand cDNA molecules hybridized to mRNA molecules; (ii) contacting the mRNA:cDNA hybrids with an enzyme comprising RNase H activity (e.g., to induce random nicking of the mRNA), thereby producing mRNA fragments hybridized to the first strand cDNA molecules; and (iii) contacting the mRNA fragments with a DNA-dependent DNA polymerase, thereby extending the mRNA fragments in a template-directed polymerase reaction, wherein the template is the first strand cDNA polynucleotide and forming the double-stranded cDNA molecules.

In some cases, the RNA-dependent DNA polymerase exhibits RNase H activity, and contacting the mRNA:cDNA hybrids with the enzyme having RNase H activity is performed by incubating the mRNA:cDNA hybrids in the presence of the RNA-dependent DNA polymerase to thereby produce the mRNA fragments hybridized to the first strand cDNA molecules. Additionally, or alternatively, contacting the mRNA:cDNA hybrids with the enzyme comprising RNase H activity can be performed by contacting the mRNA:cDNA hybrids with an enzyme that is structurally different from the RNA-dependent DNA polymerase.

In some embodiments, the variable length barcode tagged double stranded target nucleic acid molecules are variable length barcode tagged fragments of genomic DNA, or amplicons thereof. For example, genomic DNA can be provided, contacted with transposase to fragment and introduce transposon end compositions, and then the fragments can be covalently linked to variable length barcode tags by ligation and/or polymerization (e.g., polymerization with primers containing a random primer 3' region and a variable length barcode tag region). In some cases, the fragments are then amplified after contact with transposase (e.g., before linking of variable length barcode tags), and/or after covalently linking variable length barcode tags. Alternatively, the genomic DNA or amplicons thereof, can be fragmented by chemical, physical, or enzymatic means, covalently linked to variable length barcode tags by ligation and/or polymerization, and then contacted with transposase to further fragment and introduce transposon end compositions. In some cases, the genomic fragments are then amplified before covalently linking variable length barcode tags, after covalently linking variable length barcode tags (e.g., before contact with transposase), and/or after contact with transposase.

In embodiments wherein amplification is performed after contacting with transposase, amplification can be performed under conditions such that a pre-amplification "gap-fill" reaction to fill in a gap between a transferred strand and a target nucleic acid molecule is not performed. In some embodiments, it can be advantageous to reduce or eliminate the "gap-filling" by one or more DNA-dependent DNA polymerase in a reaction mixture containing amplification primers and tagmentase products. For example, increased specificity can be achieved by reducing or eliminating extension of the 3' end of the first strand cDNA molecule (e.g., templated by the transferred strand attached to the 5' end of the second strand cDNA molecule that is hybridized to the first strand cDNA) prior to the first cycle of PCR amplification with amplification primers. This is particularly advantageous when at least some (e.g., half) of the target nucleic acids include adapters that are not transposase related (such as cDNA adapters).

Accordingly, in some examples, the reaction mixture containing tagmentase products is held at a temperature that is not permissive for polymerase-mediated extension (e.g., 0, 4, 8, 10, 15, or 25° C.) until the reaction mixture is transferred to conditions suitable for a denaturation step (e.g., 90° C. or 95° C.) in an amplification (e.g., PCR) reaction. Alternatively, or additionally, the reaction mixture can contain a hot-start DNA polymerase, or contain a hot-start DNA polymerase and no other substantial DNA polymerase enzyme activity. Thus, polymerase mediated extension substantially occurs after the initial denaturing step of PCR. Additionally, or alternatively, an essential component of an amplification reaction (e.g., the polymerase or dNTPs) can be added to the reaction mixture after it has been equilibrated to a denaturing temperature.

In some embodiments, variable length barcode tagged target genomic DNA molecules are produced by hybridizing a plurality of first primers that comprise the variable length barcode tag and a genomic DNA targeting region with a plurality of genomic DNA molecules comprising at least a portion of the target nucleic acid molecule sequence, and extending the primers with a DNA-dependent DNA polymerase, thereby producing the variable length barcode tagged target genomic DNA molecules. In some cases, the genomic DNA molecules are amplified before producing the variable length barcode tagged target genomic DNA molecules, and/or after producing the variable length barcode tagged target genomic DNA molecules.

In some cases, the method of covalently linking a plurality of variable length barcode tags to a plurality of target nucleic acid molecules is performed under conditions sufficient to produce tagged target nucleic acid molecules having at least 5 different variable length barcode tag lengths or sequences, or the combination thereof. For example, the covalently linking can be performed under conditions sufficient to produce a population of variable length barcode tagged target nucleic acids having at least one target nucleic acid molecule of the population covalently linked to a variable length barcode having a length of only 1 nucleotide, at least one target nucleic acid molecule of the population covalently linked to a variable length barcode having a length of only 2 nucleotides, at least one target nucleic acid molecule of the population covalently linked to a variable length barcode having a length of only 3 nucleotides, at least one target nucleic acid molecule of the population covalently linked to a variable length barcode having a length of only 4 nucleotides, and at least one target nucleic acid molecule of the population covalently linked to a variable length barcode having a length of only 5 nucleotides.

Additionally or alternatively, the covalently linking can be performed under conditions sufficient to produce a population of variable length barcode tagged target nucleic acids having at least one target nucleic acid molecule of the population covalently linked to a variable length barcode having a first sequence, at least one target nucleic acid molecule of the population covalently linked to a variable length barcode having a second different sequence, at least one target nucleic acid molecule of the population covalently linked to a variable length barcode having a third sequence that is different from the first and second, at least one target nucleic acid molecule of the population covalently linked to a variable length barcode having fourth sequence that is different from the first, second, and third, and at least one target nucleic acid molecule of the population covalently linked to a variable length barcode having a fifth sequence that is different from the first, second, third, and fourth sequences. The variable length barcode sequences may differ by the identity of the nucleotide base (e.g., two, length 1 variable length barcodes each covalently linked to a different target nucleic acid molecule, where the first variable length barcode is "A" and the second is "G"), and/or the sequences can differ by length (e.g., a length 1 variable length barcode and a length 2 variable length barcode, where the length 1 variable length barcode is "A" and the length 2 variable length barcode is "AT").

Target nucleic acid molecules can be contacted with a plurality of transposases such that a transposase fragmentation site and a covalently linked transposon end is introduced at an end of the target nucleic acid molecules. In some embodiments, two or more different transposases can be used (e.g., each transposase possessing a different transposon end sequence capable of forming a functional complex and inserting the transposon end sequence of each transposase into one or more of the target nucleic acid molecules with which it is incubated in an in vitro transposition reaction). In some embodiments, a transposase suitable for use as outlined herein includes, but is not limited to, Tn5 transposase. In some cases, the target nucleic acid molecules are contacted with a plurality of transposases, thereby introducing transposon end compositions and fragmenting the target nucleic acid molecules to produce fragments tagged at a first end, and then the fragments are covalently linked to a plurality of variable length barcode tags (e.g., at a second end). In some cases, the target nucleic acid molecules are covalently linked to a plurality of variable length barcode tags (e.g., at a first end) and then contacted with a plurality of transposases, thereby introducing transposon end compositions and fragmenting the target nucleic acid molecules to produce fragments tagged with the variable length barcode tag and the transposon end composition.

In some embodiments, covalently linking of variable length barcode tags and transposase tagmentation produces a plurality of uniquely tagged target nucleic acid molecules, wherein individual uniquely tagged target nucleic acid molecules of the plurality comprise: (i) the variable length barcode tag at a first end; and (ii) the transposase fragmentation site and transposon end at a second end, wherein a combination of: (i) and (ii) together in the uniquely tagged individual target nucleic acid molecules of the plurality comprise a unique molecular barcode that is unique as compared to all other uniquely tagged individual target nucleic acid molecules of the plurality that have an identical sequence of at least 25 contiguous nucleotides between the variable length barcode tag and the transposase fragmentation site in the reaction mixture. For example, the foregoing (i) and (ii) together can comprise a unique molecular barcode that is unique as compared to all other uniquely tagged individual target nucleic acid molecules of the plurality that have an identical sequence of at least 25, 50, 75, 100, 120, 150, 175, 200, 250, 300, 350, 400, 450, 500, or 750 contiguous nucleotides between the variable length barcode tag and the transposase fragmentation site in the reaction mixture.

Typically, the methods described herein are applicable to a complex sample containing a large number of different target nucleic acid molecule sequences. In some embodiments, the methods described herein are applicable for the identification and/or detection of low frequency (<1%, <0.5%, or 0.1%) mutations in different target nucleic acid molecules. In another embodiment, the methods described herein are applicable for the quantitation of low level (e.g., subpicogram) amounts of target nucleic acid molecules from a single cell. For example, the methods can be performed in a reaction mixture containing, containing about, containing at least, or containing at least about 100; 200; 300; 400; 500; 600; 700; 800; 900; 1,000; 2,500; 5,000; 7,500; 10,000; 15,000; 25,000; or 30,000 target nucleic acid molecules of different sequences. In some embodiments, the reaction mixture is a reaction mixture of target nucleic acid molecules from a single cell. In another embodiment, the reaction mixture is a reaction mixture of target nucleic acid molecules from a plurality of cells. Similarly, the methods described herein are applicable to a complex sample containing a large number of target nucleic acid molecules. For example, the methods can be performed in a reaction mixture containing, containing about, containing at least, or containing at least about 10,000; 25,000; 50,000; 75,000; 100,000; 150,000; 200,000; 250,00; or 300,000 target nucleic acid molecules. In some cases, the reaction mixture is a reaction mixture of target nucleic acid molecules from a single cell. In some cases, the reaction mixture is a reaction mixture of target nucleic acid molecules from a small number of cells (e.g., a biopsy). For example, the reaction mixture can be a reaction mixture of target nucleic acids from 2, 3, 4, 5, 10, 15, 20, 30, 50, 75, 100, 150, 200, 250, 300, 350, 400, 500, or 1,000 cells or from 10-30, 10-50, 10-100, 10-250, 10-500, 25-100, 25-1,000, 25-750, 25-500, 25-250, 50-100, 50-1,000, 50-750, 50-500, or 50-250 cells.

In some embodiments, the plurality of uniquely tagged individual target nucleic acid molecules (e.g., uniquely tagged by combination of variable length barcode tag and transposase fragmentation site) further contain a cell barcode. In some cases, the plurality of uniquely tagged individual target nucleic acid molecules are cDNA and the cell barcode is 3' of a poly-A region and/or 5' of a poly-T region. In some cases, the cell barcodes are covalently linked to the uniquely tagged individual target nucleic acid molecules during the covalent linking of the variable length barcode tag. In some cases, the cell barcodes are covalently linked to the uniquely tagged individual target nucleic acid molecules during the contacting with transposase. In some cases, the cell barcodes are introduced in a separate step, such as before covalently linking of variable length barcode tags, after covalently linking of variable length barcode tags, before contact with transposase, or after contact with transposase.

In the foregoing embodiments, aspects, and examples, the target nucleic acids (e.g., variable length barcode tagged target nucleic acids or untagged target nucleic acids) can be contacted with a transposase having a transposon end that includes the sequence of

GTCTCGTGGGCTCGG, (SEQ ID NO: 2)

TCGTCGGCAGCGTC, (SEQ ID NO: 3)

AGATGTGTATAAGAGACAG, (SEQ ID NO: 4)

TCGTCGGCAGCGTCAGATGTGTATAAGAGACAG, (SEQ ID NO: 5)

GTCTCGTGGGCTCGGAGATGTGTATAAGAGACAG, (SEQ ID NO: 6)

CTGTCTCTTATACACATCT, (SEQ ID NO: 7)

or a combination of any two, three, four, five, six, or all thereof.

III. Methods of Estimating a Number of Target Nucleic Acid Molecules in a Sample Described herein are methods of estimating an absolute number of target nucleic acid molecules in a sample by high-throughput sequencing. Generally, the methods include obtaining a plurality of sequence reads from a plurality of uniquely tagged target nucleic acids or portions thereof, identifying duplicates (e.g., amplification copies) by the presence of a combination of transposase fragmentation site and variable length barcode tag, and counting sequence reads that are not duplicates. The presence of an identical sequence between the transposase fragmentation site and the variable length barcode tag provides a way to identify duplicates, and thus exclude said duplicates from the absolute number of target nucleic acid molecules in the sample. Furthermore, the presence of a cell barcode ($BC_c$) in the tagged target nucleic acids also provides a way to determine the absolute number of target nucleic acid molecules in a sample derived from a plurality of cells.

In some embodiments, the method includes: (A) providing a reaction mixture, wherein the reaction mixture comprises a plurality of uniquely tagged target nucleic acid molecules (e.g., from a single cell, or a biological or environmental sample) comprising: (i) a variable length barcode tag at a first end; and (ii) a transposase fragmentation site and transposon end at a second end; and wherein a combination of: (i) and (ii) together comprise a unique molecular barcode that is unique as compared to all other uniquely tagged target nucleic acid molecules having an identical sequence between the variable length barcode tag and the transposase fragmentation site in the reaction mixture. In some embodiments, the reaction mixture is amplified after (A) and before sequencing. The method can further include: (B) obtaining a plurality of sequence reads, wherein the sequence reads comprise one or more of the following: a sequence of the variable length barcode tag, a sequence of a portion of the target nucleic acid between the variable length barcode tag and the transposase fragmentation site, and a sequence of the fragmentation site. The method can further include: (C) counting a number of target nucleic acid molecules having an identical sequence between the variable length barcode tag and the transposase fragmentation, but different variable length barcode tags and/or transposase fragmentation sites, thereby estimating the absolute number of target nucleic acid molecules in the reaction mixture.

In another embodiment, the method includes: (A) providing a reaction mixture, wherein the reaction mixture comprises a plurality of uniquely tagged target nucleic acid molecules from a single cell comprising: (i) a variable length barcode tag at a first end; and (ii) a transposase fragmentation site and transposon end at a second end; and wherein a combination of: (i) and (ii) together comprise a unique molecular barcode that is unique as compared to all other uniquely tagged target nucleic acid molecules having an identical sequence between the variable length barcode tag and the transposase fragmentation site in the reaction mixture. In some embodiments, the reaction mixture is amplified after (A) and before sequencing. The method can further include: (B) obtaining a plurality of sequence reads, wherein the sequence reads comprise one or more of the following: a sequence of the variable length barcode tag, a sequence of a portion of the target nucleic acid between the variable length barcode tag and the transposase fragmentation site, and a sequence of the fragmentation site. The method can further include: (C) counting a number of target nucleic acid molecules having an identical sequence between the variable length barcode tag and the transposase fragmentation, but different variable length barcode tags and/or transposase fragmentation sites, thereby estimating the absolute number of target nucleic acid molecules in the single cell.

In yet another embodiment, the method includes: (A) providing a reaction mixture, wherein the reaction mixture comprises a plurality of uniquely tagged target nucleic acid molecules in a plurality of fluid partitions comprising: (i) a variable length barcode tag at a first end; and (ii) a transposase fragmentation site and transposon end at a second end; and wherein a combination of: (i) and (ii) together comprise a unique molecular barcode that is unique as compared to all other uniquely tagged target nucleic acid molecules having an identical sequence between the variable length barcode tag and the transposase fragmentation site in the reaction mixture. In some embodiments, the reaction mixture containing the plurality of fluid partitions is amplified after (A) and before sequencing. The method can further include: (B) obtaining a plurality of sequence reads, wherein the sequence reads comprise one or more of the following: a sequence of the variable length barcode tag, a sequence of a portion of the target nucleic acid between the variable length barcode tag and the transposase fragmentation site, and a sequence of the fragmentation site. The method can further include: (C) counting a number of target nucleic acid molecules having an identical sequence between the variable length barcode tag and the transposase fragmentation, but different variable length barcode tags and/or transposase fragmentation sites, thereby estimating the absolute number of target nucleic acid molecules in the reaction mixture.

In some embodiments, the foregoing uniquely tagged target nucleic acid molecules having the variable length barcode tag and transposase fragmentation site are provided by performing one or more of the methods described in section II above. For example, variable length barcode tags can be attached by polymerase-mediated primer extension and the tagged target nucleic acids can then be contacted with a transposase.

In some embodiments, the method includes performing a computer implemented method in which a computer program product containing non-transitory machine readable code is executed by a computer system to analyze data comprising a plurality of sequence reads produced in (B), thereby estimating an absolute number of target nucleic acid molecules in a sample. In some cases, the non-transitory machine readable medium storing program code causes a computer system to implement a method for estimating a number of target nucleic acid molecules in a reaction mixture using: (A) a sequence of the target nucleic acid; and (i) a variable length barcode tag at a first end of the target nucleic acid; and, (ii) a transposase fragmentation site and transposon end at a second end of the target nucleic acid to identify and estimate the absolute number of individual molecules of the target nucleic acid in the reaction mixture.

In some cases, the program code contains: code for obtaining sequencing reads of a plurality of, e.g., amplified, target nucleic acids having the variable length barcode tag and the transposase fragmentation site. In some cases, the program code contains: code for identifying a plurality of unique molecular identifiers (UMIs) from a combination of the variable length barcode tag and transposase fragmentation site; and code for counting a number of target nucleic acid molecules having such unique molecular identifiers.

IV. Compositions

Described herein are various reaction mixtures resulting from one or more of the foregoing methods, or suitable for performing one or more of the foregoing methods. Such reaction mixtures can include, without limitation, sequencing libraries, variable length barcode tags (e.g., as a component of primer(s) or adapter(s)), and/or variable length barcode tagged target nucleic acids.

In some embodiments, the reaction mixture can contain a plurality of uniquely tagged target nucleic acid molecules, wherein the plurality of uniquely tagged target nucleic acid molecules comprise: (i) a variable length barcode tag at a first end; and (ii) a transposase fragmentation site and transposon end at a second end; and wherein a combination of: (i) and (ii) together comprise a unique molecular barcode that is unique as compared to all other uniquely tagged target nucleic acid molecules having an identical sequence between the variable length barcode tag and the transposase fragmentation site in the reaction mixture. In some embodiments, the reaction mixture can contain at least 1000 different uniquely tagged target nucleic acid molecules. In some embodiments, the reaction mixture can contain, or contain at least 500; 5,000; 7,500; 10,000; 15,000; 25,000; 30,000; 50,000; 75,000; 100,000; 150,000; 200,000; 250,00; or 300,000 uniquely tagged target nucleic acid molecules. In some embodiments, the reaction mixture further contains amplification products of the uniquely tagged target nucleic acid molecules.

Although the foregoing invention has been described in some detail by way of illustration and example for purposes of clarity of understanding, one of skill in the art will appreciate that certain changes and modifications may be practiced within the scope of the appended claims. All patents, patent applications, and other publications, including GenBank Accession Numbers, Entrez Gene IDs, and publications referred to by pubmed ID (PMID), cited in this application are incorporated by reference in the entirety for all purposes.

What is claimed is:

1. A method of producing a reaction mixture comprising uniquely tagged target nucleic acid molecules, the method comprising:
   a) forming a plurality of double-stranded variable length barcode-tagged target cDNA molecules wherein the forming comprises (i) hybridizing a plurality of individual primers with a plurality of mRNA molecules, wherein the individual primers comprise a barcode, a variable length barcode tag, and a 3' poly-T region, and extending the primers with an RNA-dependent DNA polymerase, thereby producing a plurality of double-stranded mRNA:cDNA hybrids with first strand cDNA molecules hybridized to mRNA molecules; (ii) contacting the mRNA:cDNA hybrids with an enzyme comprising RNase H activity to induce random nicking of the mRNA, thereby producing mRNA fragments hybridized to the first strand cDNA molecules; and (iii) contacting the mRNA fragments with a DNA-dependent DNA polymerase, thereby extending the mRNA fragments in a template-directed polymerase reaction, wherein the template is the first strand cDNA polynucleotide and forming the double-stranded cDNA molecules,
   wherein the variable length barcode tags consist of from 0-10 nucleotides and double-stranded variable length barcode-tagged target cDNA molecules comprise a single variable length barcode tag and the plurality comprises at least 5 different variable length barcode tag lengths and/or sequence(s); and
   b) contacting the double-stranded variable length barcode-tagged target cDNA molecules with a plurality of transposases, such that a transposase fragmentation site and a covalently linked transposon end is introduced at a second end of the individual double-stranded variable length barcode-tagged target cDNA molecules of the plurality, thereby producing a plurality of uniquely tagged target nucleic acid molecules, wherein individual uniquely tagged target nucleic acid molecules of the plurality comprise:
   i) the variable length barcode tag at a first end; and
   ii) the transposase fragmentation site and transposon end at the second end,
   wherein a combination of: i) and ii) together in the uniquely tagged individual target nucleic acid molecules of the plurality comprise a unique molecular barcode that is unique as compared to all other uniquely tagged individual target nucleic acid molecules of the plurality that have an identical sequence of at least 25 contiguous nucleotides between the variable length barcode tag and the transposase fragmentation site in the reaction mixture.

2. The method of claim 1, further comprising, after the contacting, amplifying the uniquely tagged target nucleic acid molecules without performing gap-filling.

3. The method of claim 1, wherein the reaction mixture comprises between 1 and 10,000 target nucleic acid molecules of different sequence.

4. The method of claim 1, wherein the reaction mixture comprises a plurality of fluid partitions comprising mRNA molecules from a single cell.

5. The method of claim 1, wherein a) is performed in a reaction mixture wherein the mRNA molecules are from a single cell or wherein a) and b) are performed in a reaction mixture wherein the mRNA molecules are from a single cell.

6. The method of claim 1, wherein the variable length barcode tag consists of from 0-10 nucleotides of a single nucleic acid sequence, wherein at least a portion of variable length barcode tags contain at least 1 nucleotide.

7. The method of claim 1, wherein the transposon end comprises from 5' to 3' GTCTCGTGGGCTCGG (SEQ ID NO:2); TCGTCGGCAGCGTC (SEQ ID NO:3); AGATGTGTATAAGAGACAG (SEQ ID NO:4); TCGTCGGCAGCGTCAGATGTGTATAAGAGACAG (SEQ ID NO:5) or GTCTCGTGGGCTCGGAGATGTGTATAAGAGACAG (SEQ ID NO:6).

8. The method of claim 1, wherein the transposon end comprises two complementary nucleotide sequences comprising from 5' to 3' AGATGTGTATAAGAGACAG (SEQ ID NO: 4) and from 5' to 3' CTGTCTCTTATACACATCT (SEQ ID NO:7); TCGTCGGCAGCGTCAGATGTGTATAAGAGACAG (SEQ ID NO: 5) and from 5' to 3' CTGTCTCTTATACACATCT (SEQ ID NO:7); or GTCTCGTGGGCTCGGAGATGTGTATAAGAGACAG (SEQ ID NO: 6) and from 5' to 3' CTGTCTCTTATACACATCT (SEQ ID NO:7).

\* \* \* \* \*